US010577314B2

(12) United States Patent
Pichai et al.

(10) Patent No.: US 10,577,314 B2
(45) Date of Patent: Mar. 3, 2020

(54) PROCESS FOR PRODUCING METHYL MERCAPTAN FROM DIMETHYL SULFIDE

(71) Applicant: Novus International, Inc., St. Charles, MO (US)

(72) Inventors: Puvin Pichai, Friendswood, TX (US); James Rolston, Friendswood, TX (US); Stephan Schubert, Leverkusen (DE); Leslaw Mleczko, Leverkusen (DE); Jens Assmann, Leverkusen (DE); Edwin Gross-Hardt, Leverkusen (DE); Pankaj Ajmera, Muskegon, MI (US)

(73) Assignee: Novus International, Inc., St. Chares, MO (US)

( * ) Notice: Subject to any disclaimer, the term of this patent is extended or adjusted under 35 U.S.C. 154(b) by 0 days.

(21) Appl. No.: 15/604,995

(22) Filed: May 25, 2017

(65) Prior Publication Data

US 2017/0342028 A1  Nov. 30, 2017

Related U.S. Application Data

(60) Provisional application No. 62/343,385, filed on May 31, 2016.

(51) Int. Cl.
*C07C 319/06* (2006.01)

(52) U.S. Cl.
CPC .......... *C07C 319/06* (2013.01); *Y02P 20/582* (2015.11)

(58) Field of Classification Search
CPC ............................ C07C 319/06; Y02P 20/582
See application file for complete search history.

(56) References Cited

U.S. PATENT DOCUMENTS

| | | | |
|---|---|---|---|
| 2,214,859 A | 9/1940 | Maude | |
| 2,816,146 A | 4/1953 | Doumani | |
| 2,667,515 A | 1/1954 | Beach | |
| 2,831,031 A | 2/1954 | Binning | |
| 2,820,062 A | 1/1958 | Folkins | |
| 2,829,171 A * | 4/1958 | Doumani | C07C 319/08 428/23 |
| 2,863,725 A | 12/1958 | Maude | |
| 3,081,353 A * | 3/1963 | Forni | C07C 321/00 568/71 |
| 3,935,276 A | 1/1976 | Biola | |
| 4,005,149 A | 1/1977 | Kubicek | |
| 4,059,636 A | 11/1977 | Kubicek | |
| 4,069,636 A | 1/1978 | Kessler | |
| 4,313,006 A | 1/1982 | Hager | |
| 4,396,778 A | 8/1983 | Hager | |
| 4,665,242 A | 5/1987 | Boulinguiez | |
| 5,453,543 A | 9/1995 | Gemon | |
| 5,733,836 A | 3/1998 | Stinn | |
| 5,847,223 A | 12/1998 | Ponceblanc | |
| 5,852,219 A | 12/1998 | Sauer | |
| 5,855,230 A | 1/1999 | Guala | |
| 5,866,721 A | 2/1999 | Hofen | |
| 5,886,230 A | 3/1999 | Hofen | |
| 5,977,011 A | 11/1999 | Sauer | |
| 6,084,135 A | 7/2000 | Wachs | |
| 6,166,263 A | 12/2000 | Etzkorn | |
| 6,515,187 B1 | 2/2003 | Schon | |
| 7,368,611 B2 | 5/2008 | Barth | |
| 7,399,893 B2 | 7/2008 | Hasenberg | |
| 7,569,731 B2 | 8/2009 | Yang | |
| 7,576,243 B2 | 8/2009 | Barth | |
| 7,582,800 B2 | 9/2009 | Redlingshoefer | |
| 7,604,788 B2 | 10/2009 | Moller | |
| 7,645,906 B2 | 1/2010 | Hasenberg | |
| 7,687,667 B2 | 3/2010 | Brand | |
| 7,723,261 B2 | 5/2010 | Barth | |
| 7,736,618 B2 | 6/2010 | Redlingshoefer | |
| 7,759,523 B2 | 7/2010 | Redlingshofer | |
| 7,833,508 B2 | 11/2010 | Redlingshofer | |
| 7,833,929 B2 | 11/2010 | Yang | |
| 7,871,594 B2 | 1/2011 | Wolfert | |
| 7,994,366 B2 | 8/2011 | Barth | |
| 8,008,530 B2 | 8/2011 | Redlingshofer | |
| 8,022,254 B2 | 9/2011 | Redlingshofer | |
| 8,372,780 B2 | 2/2013 | Redlingshofer | |
| 8,426,648 B2 | 4/2013 | Barre | |
| 8,551,442 B2 | 10/2013 | Umino | |
| 8,580,208 B2 | 11/2013 | Woelfert | |
| 8,609,576 B2 | 12/2013 | Redlingshoefer | |
| 9,346,677 B2 | 5/2016 | Metheral | |
| 9,421,511 B2 | 8/2016 | Finkeldei | |
| 9,440,208 B2 | 9/2016 | Finkeldei | |
| 9,630,843 B2 | 4/2017 | Finkeldei | |
| 2005/0080295 A1 | 4/2005 | Redlingshofer | |
| 2008/0200730 A1 * | 8/2008 | Barth | C07C 319/06 568/70 |
| 2010/0094059 A1 | 4/2010 | Yang | |
| 2010/0286448 A1 | 11/2010 | Yang | |

FOREIGN PATENT DOCUMENTS

| | | |
|---|---|---|
| DE | 1193038 | 5/1965 |
| EP | 104507 | 4/1984 |
| FR | 2477538 | 9/1981 |
| GB | 2016468 | 9/1979 |
| JP | 58159456 | 9/1983 |
| WO | 2005040082 | 5/2005 |
| WO | 2017/210070 | 12/2017 |

OTHER PUBLICATIONS

International Search Report and Written Opinion dated Aug. 14, 2017 from related International application No. PCT/US2017/034391, 9 pp.
Koshelev, Catalytic Conversion of Dimethylsulfide to Methylmercaptan, React. Kinet. Catal. Lett., 1985, vol. 27, No. 2, pp. 387-391.
Mashkin, Kinetic Studies of Methylmercaptan Production from Dimethyl Sulfide and H2S, React. Kinet. Catal. Lett., 1992, vol. 46, No. 1, pp. 187-792.

(Continued)

*Primary Examiner* — Rosalynd A Keys
(74) *Attorney, Agent, or Firm* — Polsinelli PC (57) ABSTRACT

The present invention generally relates to the manufacture of methyl mercaptan using recycled dimethyl sulfide. In particular, the invention relates to a process for the continuous production of methyl mercaptan via the catalytic conversion of dimethyl sulfide using a non-promoted $Al_2O_3$ catalyst at low temperatures.

12 Claims, 4 Drawing Sheets

(56) References Cited

OTHER PUBLICATIONS

Wang, Promotion function of Co to the Supported Catalyst K2MoO4 for the Synthesis of Methanethiol from H2S-Containing Syngas, Chemical Abstracts Service Jun. 26, 2003, published in the Journal of Xiamen University (Natural Science) Jan. 2003, vol. 42, No. 1. [English translation of Japanese language article].

Erdohelyi, Catalytic reaction of methane with carbon dioxide over supported palladium, Applied Catalysis A: General, 1994, vol. 108, pp. 205-219.

Erdohelyi, Activation of CH4 and Its Reaction with CO2 over Supported Rh Catalysts, Journal of Catalysis, 1993, vol. 141, pp. 287-299.

Yang, Study of the supported K2MoO4 catalyst for methanethiol synthesis by one step from high H2S-containing syngas, Catalysis Letters, 2001, vol. 74, No. 3-4, pp. 221-225.

Barrault, Synthesis of Methyl Mercaptan from Carbon Oxides and H2S with Tungsten-Alumina Catalysts, Applied Catalysis, 1987, vol. 33, pp. 309-330.

Folkins, Synthesis of Mercaptans, I&EC Process Design and Development, Oct. 1962, vol. 1, No. 4, pp. 271-276.

* cited by examiner

PROCESS FOR PRODUCING METHYL MERCAPTAN FROM DIMETHYL SULFIDE

CROSS REFERENCE TO RELATED APPLICATIONS

This application claims the benefit of U.S. Provisional Application No. 62/343,385, filed May 31, 2016, which is hereby incorporated by reference in its entirety.

FIELD OF THE INVENTION

The invention generally relates to the manufacture of methyl mercaptan using recycled dimethyl sulfide. In particular, the invention relates to a process for the continuous production of methyl mercaptan via the catalytic conversion of dimethyl sulfide using a non-promoted $Al_2O_3$ catalyst at low temperatures.

BACKGROUND OF THE INVENTION

One route to forming methyl mercaptan (MeSH) is through the reaction of methanol (MeOH) with hydrogen sulfide ($H_2S$). This process is referred to herein as the "methanol route." The general chemical reaction that is the basis of the methanol route is as follows: $CH_3OH + H_2S \rightarrow CH_3SH + H_2O$. In industrial reactors, however, neither conversion of the reactants nor selectivity for methyl mercaptan is 100%. As used herein, the term "conversion" refers to the percentage of the initial amount of the substoichiometric reactant that is consumed in a reaction to produce methyl mercaptan and any secondary products. The part percentage of the consumed amount of the reactant which gives rise to methyl mercaptan alone is called "selectivity". Accordingly, the yield of methyl mercaptan may be calculated as follows: $yield_{MeSH} = (conversion_{Reactant})(selectivity_{MeSH})$. In particular, side reactions of the methanol route often include formation of dimethyl ether (DME) and dimethyl sulfide (DMS). In a typical, non-recycle process, the methyl mercaptan would be separated from the by-products (e.g. dimethyl sulfide and dimethyl ether) and the by-products disposed of, resulting in a loss of carbon and sulfur. This loss translates to increased methanol and hydrogen sulfide raw material costs and lower overall methyl mercaptan yield.

Methods for recovering dimethyl sulfide from the product stream, mixing the recovered dimethyl sulfide with clean hydrogen sulfide, feeding the mixture to a catalytic reactor to convert part of the dimethyl sulfide to methyl mercaptan have been described in the art but have many disadvantages—e.g. cost, complexity, low yield. Accordingly, improved methods for producing methyl mercaptan are desired.

SUMMARY OF THE INVENTION

One aspect of the present disclosure is directed to a process for producing methyl mercaptan. The process comprising reacting an influent gas stream comprising clean hydrogen sulfide and recycled dimethyl sulfide in a reactor at a temperature of about 200° C. to less than 300° C. to produce an effluent gas stream comprising methyl mercaptan, dimethyl sulfide, and hydrogen sulfide; wherein the influent gas stream comprises clean hydrogen sulfide and recycled dimethyl sulfide at a molar ratio of at least 20:1; wherein the reactor comprises a non-promoted $Al_2O_3$ catalyst and operates at a weight hourly space velocity of about 0.01 and 10.0 g dimethyl sulfide/hour/gram $Al_2O_3$; and wherein the methyl mercaptan is produced at a conversion of recycled dimethyl sulfide to methyl mercaptan of at least about 50 mol % and a selectivity for methyl mercaptan of greater than 90%.

Another aspect of the present disclosure is directed to a continuous process for producing methyl mercaptan. The process comprising (a) reacting an influent gas stream comprising clean hydrogen sulfide and recycled dimethyl sulfide in a first reactor at a temperature of about 200° C. to less than 300° C. to produce a first effluent gas stream comprising methyl mercaptan, dimethyl sulfide, and hydrogen sulfide, wherein the influent gas stream comprises clean hydrogen sulfide and recycled dimethyl sulfide at a molar ratio of at least 20:1; wherein the first reactor comprises a non-promoted $Al_2O_3$ catalyst, and operates at a weight hourly space velocity of about 0.01 and 10.0 g dimethyl sulfide/hour/gram $Al_2O_3$; and wherein the methyl mercaptan is produced at a conversion of recycled dimethyl sulfide to methyl mercaptan of at least about 50 mol % and selectivity for methyl mercaptan of greater than 90%; (b) reacting the first effluent gas stream and clean liquid methanol in a second reactor to produce a second effluent gas stream comprising methyl mercaptan, dimethyl sulfide, dimethyl ether, hydrogen sulfide, and methanol, wherein the second reactor has a catalyst comprising aluminum oxide particles doped with an alkali metal; and (c) recovering at least a portion of the dimethyl sulfide from the second effluent gas stream and recycling it to step (a).

An additional aspect of the present disclosure is directed to a continuous process for producing methyl mercaptan. The process comprising (a) reacting an influent gas stream comprising clean hydrogen sulfide and recycled dimethyl sulfide in a first adiabatic reactor at a temperature of about 200° C. to less than 300° C. to produce a first effluent gas stream comprising methyl mercaptan, dimethyl sulfide, and hydrogen sulfide, wherein the influent gas stream comprises clean hydrogen sulfide and recycled dimethyl sulfide at a molar ratio of at least 20:1; wherein the reactor comprises a non-promoted $Al_2O_3$ catalyst and operates at a weight hourly space velocity of about 0.01 and 10.0 g dimethyl sulfide/hour/gram $Al_2O_3$; and wherein the methyl mercaptan is produced at a conversion of recycled dimethyl sulfide to methyl mercaptan of at least about 50 mol % and a selectivity for methyl mercaptan of greater than 90%; (b) reacting the first effluent gas stream and clean liquid methanol in a second adiabatic reactor at a temperature of about 250° C. to about 400° C. to produce a second effluent gas stream comprising methyl mercaptan, dimethyl sulfide, dimethyl ether, hydrogen sulfide, and methanol; wherein the clean liquid methanol conversion to methyl mercaptan is at least 85 mol % and the selectivity for methyl mercaptan is greater than 90%; wherein the second adiabatic reactor has two or more catalyst stages, and the catalyst in each stage comprises aluminum oxide particles and potassium tungstate, and wherein a portion of the total amount of clean liquid methanol is introduced upstream of each catalyst stage; and (c) recovering at least a portion of the dimethyl sulfide from the second effluent gas stream and recycling it to step (a).

Other aspects and iterations of the disclosure are described in more detail below.

DETAILED DESCRIPTION

The present disclosure provides a process for producing methyl mercaptan through the following reaction: $CH_3$—S—$CH_3$+$H_2S$→2 $CH_3SH$. The process generally comprises feeding to a reactor one or more gas streams comprising clean hydrogen sulfide and recycled dimethyl sulfide, and reacting the hydrogen sulfide and dimethyl sulfide in the reactor at a temperature less than 300° C., in the presence of a non-promoted, $Al_2O_3$ catalyst, to produce an effluent gas stream comprising methyl mercaptan, dimethyl sulfide, and hydrogen sulfide. As used herein, a "clean" reactant is a reactant that has not been previously used in, or produced by, a manufacturing process for producing methyl mercaptans. In contrast, a "recycled" reactant is a reactant that has been previously used in, or produced by, a manufacturing process for producing methyl mercaptans. Via use of a hydrogen sulfide to dimethyl sulfide feed molar ratio that is at least 20:1, the recycle process can occur at low reaction temperatures while still achieving dimethyl sulfide conversion to methyl mercaptan that is at least about 50 mol %.

The recycle process described above has many advantages, particularly on an industrial scale. The lower temperature, coupled with the endothermic nature of the dimethyl sulfide cleavage reaction, also allows the use of an adiabatic reactor instead of a tubular reactor. In comparison with a tubular reactor, an adiabatic reactor is less expensive, simpler to operate, less sensitive to changes in catalyst activity, easier and faster to change catalyst, easier to debottleneck, and does not require additional utility for temperature control. Additional advantages of the recycle process include a decreased risk of catalyst deactivation and the ability to use a reasonable-sized reactor.

Additional recycled reactants can also be used in the recycle process to further improve the overall methyl mercaptan yield. For example, recycled dimethyl ether and/or recycled methanol may also be used to produce methyl mercaptan through the following reactions: $CH_3OCH_3$+$2H_2S$↔$2CH_3SH$+$H_2O$ (dimethyl ether conversion); and $CH_3OH$+$H_2S$→$CH_3SH$+$H_2O$ (methanol conversion). Advantageously, the exothermic conversion of methanol and dimethyl ether into methyl mercaptan generates sufficient heat to help maintain the reaction temperature in the reactor. It is believed this will provide more uniform operating conditions, potentially increasing the reactor performance and extending catalyst life. These advantages, however, need to be balanced against certain disadvantages identified by the inventors, in particular a decrease in the percent of dimethyl sulfide converted to methyl mercaptan. A suitable balance may be achieved by limiting the amount of recycled dimethyl ether and/or recycled methanol used in the recycle process.

This disclosure also provides a continuous process for producing methyl mercaptan using a recycle process described above. In the continuous process for producing methyl mercaptan, the effluent gas mixture from a recycle process and clean, liquid methanol are fed to a downstream reactor and reacted to produce a second effluent gas stream comprising methyl mercaptan, dimethyl sulfide, dimethyl ether, hydrogen sulfide, and methanol. After methyl mercaptan and water are removed from the second effluent gas stream, the remaining by-products (e.g. dimethyl sulfide and dimethyl ether) and unconsumed reactants (e.g. methanol and hydrogen sulfide) may be recycled to the first reactor.

Additional aspects of the above processes are described in further detail below.

I. Recycle Process

One aspect of the present disclosure is a process for producing methyl mercaptans using clean hydrogen sulfide and recycled dimethyl sulfide. As stated above, a "recycled" reactant is a reactant that has been previously used in, or produced by, a manufacturing process for producing methyl mercaptans. Typically, a recycled reactant is recycled from a manufacturing process that produces methyl mercaptan via the methanol route. However, the type of manufacturing process is not a limiting feature of the invention, provided dimethyl sulfide is a recycled reactant.

The recycle process generally comprises reacting an influent gas stream comprising clean hydrogen sulfide and recycled dimethyl sulfide in a reactor ("the recycle reactor") at a temperature of about 200° C. to less than 300° C. to produce an effluent gas stream comprising methyl mercaptan, dimethyl sulfide, and hydrogen sulfide; wherein the influent gas stream comprises clean hydrogen sulfide and recycled dimethyl sulfide at a molar ratio of at least 20:1 ("the $H_2S$:DMS feed ratio"); and wherein the recycle reactor comprises a non-promoted, $Al_2O_3$ catalyst. The influent gas stream may further comprise recycled dimethyl ether, recycled hydrogen sulfide, recycled methanol, or any combination thereof. The total amount of hydrogen sulfide (i.e., the clean hydrogen sulfide and, if any, recycled hydrogen sulfide) used in the recycle process is provided to the reactor upstream of the first catalyst stage. In this regard, when the influent gas stream comprises recycled hydrogen sulfide, the amount of clean hydrogen sulfide may be reduced to account for the contribution of the recycled hydrogen sulfide.

(a) Clean Hydrogen Sulfide

The term "clean hydrogen sulfide" refers to hydrogen sulfide that has not been previously used in a manufacturing process for producing methyl mercaptans (i.e., not recycled). Typically, clean hydrogen sulfide is provided to the recycle reactor as a compressed gas. Clean hydrogen sulfide may be provided from a hydrogen sulfide reactor connected upstream of the recycle reactor. Alternatively, clean hydrogen sulfide gas may be supplied from storage (e.g., cylinders or other form of containment). Although a clean hydrogen sulfide gas stream consists essentially of hydrogen sulfide gas, minor impurities may be present.

(b) Recycled Reactants

Recycled reactants are either by-products of or unconsumed reactants from a manufacturing process for methyl mercaptan that have been recovered and recycled for re-use. In this regard, the recycled reactants used in the recycle process can and will vary but minimally include recycled dimethyl sulfide. Recycled reactants used in the recycle process may also include, but are not limited to, other dialkyl sulfides (e.g., diethyl sulfide, dipropyl sulfide, etc.), dialkyl polysulfide compounds (e.g., dimethyl disulfide, dimethyl trisulfide, dimethyl tetrasulfide, dithiapentanes), alkyl ether compounds (e.g., dimethyl ether), hydrogen sulfide, and methanol. Recycled reactants recovered from a manufacturing process that produces methyl mercaptan via the methanol route may include, in addition to dimethyl sulfide, recycled hydrogen sulfide, recycled methanol, and/or recycled dimethyl ether.

Recycled reactants are fed to the recycle reactor as a gas (a "recycle gas") and may be provided as one or more gas streams (a "recycle gas stream"). However, one or more recycled reactants may be initially provided as a liquid stream that is atomized and combined with a gas stream, or converted to a gas, before entering the reactor. In some embodiments, one recycle gas stream is provided comprising recycled dimethyl sulfide. In other embodiments, one recycle gas stream is provided comprising recycled dimethyl sulfide and recycled hydrogen sulfide. In still other embodiments, one recycle gas stream is provided comprising recycled dimethyl sulfide, recycled hydrogen sulfide, recycled methanol, and recycled dimethyl ether. In alternative embodiments, a first recycle gas stream is provided comprising recycled dimethyl sulfide and recycled methanol, and a second recycle gas stream is provided comprising recycled hydrogen sulfide and recycled dimethyl ether. In yet another alternative, one recycle gas stream is provided consisting of dimethyl sulfide.

The amount of each recycled reactant provided to the recycle reactor may vary depending upon reaction conditions (e.g., temperature, weight hourly space velocity, etc.), provided the $H_2S$:DMS feed ratio is at least 20:1. For example, the $H_2S$:DMS feed ratio may be 20:1, 25:1, 30:1, 35:1, 40:1, 45:1, 50:1, 55:1, 60:1, or higher. In some embodiments, recycled dimethyl sulfide is the only recycle reactant provided to the recycle other. In embodiments where recycled methanol and/or recycled dimethyl ether are provided to the recycled reactor, the molar ratio of methanol or dimethyl ether to dimethyl sulfide is minimized. In certain embodiments, the molar ratio of methanol or dimethyl ether to dimethyl sulfide is less than 2.3, preferably less than 1.0, more preferably less than 0.3. In embodiments where recycled hydrogen sulfide is provided to the recycled reactor, the amount of clean hydrogen sulfide gas may be reduced proportionately to achieve the desired $H_2S$:DMS feed ratio.

(c) Reactor and Catalyst

Although not required, the influent recycle gas streams are typically combined with the clean hydrogen sulfide gas stream before entering the recycle reactor via one or more inlet. In this manner, the clean hydrogen sulfide feed can be adjusted based on the amount, if any, of recycled hydrogen sulfide in a recycled gas stream. Alternatively, a clean hydrogen sulfide gas stream and one or more recycled gas streams may be fed into the recycle reactor via separate inlets. In another alternative, a clean hydrogen sulfide gas stream is combined with a recycled gas stream comprising recycled hydrogen sulfide before entering the recycle reactor, which is then fed into the recycle reactor via one inlet and one or more additional recycled gas streams are fed into the recycle reactor via additional inlet(s).

Although it is common practice in the art to use catalysts comprising a promoter for maximal methyl mercaptan yield and selectivity, the recycle reactor does not contain a catalyst comprising a promoter. Rather, the recycle reactor contains a non-promoted $Al_2O_3$ catalyst. Stated another way, the catalyst is an aluminum oxide particle that is not impregnated with a promoter. The alumina is typically present in the form of a transition alumina, preferably as gamma-alumina. The catalyst is generally in the solid phase and may be in a variety of forms such as pellets, spheres, or rings. The catalyst has an alumina surface area between 100 $m^2/g$ and 500 $m^2/g$, and particle size of about 1.5 mm to about 5 mm. In some embodiments, catalyst has an alumina surface area between about 150 $m^2/g$ and 500 $m^2/g$, between about 200 $m^2/g$ and 500 $m^2/g$, or between 250 $m^2/g$ and 500 $m^2/g$. In other embodiments, a catalyst has an alumina surface area between about 100 $m^2/g$ and 450 $m^2/g$, between about 150 $m^2/g$ and 450 $m^2/g$, or between about 200 $m^2/g$ and 450 $m^2/g$. In an exemplary embodiment, a catalyst has an alumina surface area between about 200 $m^2/g$ and about 250 $m^2/g$. The pore size of the particles may range between about 2 nm to about 20 nm, or between about 5 nm and 15 nm. Alternatively, alumina particles with a bimodal pore size distribution may be used. For example, a catalyst may contain particles with a pore size of between 2 nm to 20 nm and particles with a pore size between about 50 nm to about 1 μm. The catalyst may optionally be mixed with inert carriers such as silica, silicates, titanium dioxide, or zirconium oxides.

Generally speaking, the type of reactor used in the recycle process is not critical. In this regard, the recycle reactor may be a fluidized bed reactor. Alternatively, a fixed-bed or a multi-tube tubular reactor with liquid coolant passed through the shell may be used in the recycle process. In typical operation of a tubular reactor, a heat transfer fluid, such as a molten salt bath, may be used to transfer heat during methyl mercaptan production. Any transfer fluid used in this process should be stable at the temperatures of reaction. Although the type of reactor is not critical for the recycle process, an adiabatic reactor is preferred for the reasons discussed above. The adiabatic reactor may be a single stage (n=1) or a multi-stage (n>1) adiabatic reactor. In typical operation of an adiabatic reactor, temperature rises from inlet to outlet of each stage. A skilled artisan will appreciate that the length of each stage and/or amount of catalyst per stage, as well as the number of stages, can influence the temperature rise per stage.

The reaction conditions, namely temperature, pressure, and weight hourly space velocity, in the recycle reactor can and will vary. In this regard, the temperature in the recycle reactor is generally less than 300° C. For example, the temperature in the recycle reactor may range from about 200° C. to less than 300° C. In various embodiments, the temperature may be about 200° C., about 210° C., about 220° C., about 230° C., about 240° C., about 250° C., about 260° C., about 270° C., about 280° C., about 290° C., or about 295° C. In other embodiments, the temperature may be about 220° C. to less than 300° C., about 230° C. to less than 300° C., about 240° C. to less than 300° C., or about 250° C. to less than 300° C. In still other embodiments, the temperature may be between about 200° C. to about 275° C., between about 200° C. to about 250° C., or between about 225° C. to about 250° C. In still other embodiments, the temperature of the first reactor may be between about 200° C. to about 280° C., between about 220° C. to about 280° C., between about 240° C. to about 280° C., between about 220° C. to about 250° C., or between about 240° C. to about 270°

C. The temperature at the reactor inlet and outlet may be different and can and will vary, particularly when the reactor is an adiabatic reactor.

The overall operating pressure of the recycle reactor also can and will vary. A suitable operating pressure of the recycle reactor is generally about 40 bar or less. For example, the operating pressure of the recycle reactor may be about 1 bar, about 5 bar, about 10 bar, 15 bar, about 20 bar, about 25 bar, or about 30 bar. Alternatively, the operating pressure of the recycle reactor may be between about 10 and about 40 bar. In certain embodiments, the operating pressure of the recycle reactor may be between about 10 and about 20 bar.

The weight hourly space velocity (WHSV) within the reactor also can and will vary. As used herein "weight hourly space velocity" refers to the hourly mass feed flow rate per catalyst mass. It is calculated by dividing the weight of feed flowing per hour by the unit weight of the catalyst (e.g., grams DMS per hour/grams $Al_2O_3$). In one embodiment, the weight hourly space velocity may range from about 0.01 to about 10.0 g DMS/h/g $Al_2O_3$. In another embodiment, the weight hourly space velocity may range from about 0.01 to about 5.0 g DMS/h/g $Al_2O_3$, about 0.01 to about 1.0 g DMS/h/g $Al_2O_3$, or about 0.01 to about 0.05 g DMS/h/g $Al_2O_3$. In an alternative embodiment, the weight hourly space velocity may range from about 0.05 to about 10.0 g DMS/h/g $Al_2O_3$, about 0.05 to about 0.5 g DMS/h/g $Al_2O_3$, or about 0.05 to about 1.0 g DMS/h/g $Al_2O_3$. In a different embodiment, the weight hourly space velocity may range from about 1.0 to about 7.5 g DMS/h/g $Al_2O_3$, or about 1.0 to about 5.0 g DMS/h/g $Al_2O_3$. In various embodiments, the gas hourly space velocity may be about 0.01 g DMS/h/g $Al_2O_3$, about 0.015 g DMS/h/g $Al_2O_3$, about 0.02 g DMS/h/g $Al_2O_3$, about 0.025 g DMS/h/g $Al_2O_3$, about 0.03 g DMS/h/g $Al_2O_3$, about 0.035 g DMS/h/g $Al_2O_3$, about 0.04 g DMS/h/g $Al_2O_3$, about 0.045 g DMS/h/g $Al_2O_3$, about 0.05 g DMS/h/g $Al_2O_3$, about 0.055 g DMS/h/g $Al_2O_3$, about 0.06 g DMS/h/g $Al_2O_3$, about 0.065 g DMS/h/g $Al_2O_3$, about 0.07 g DMS/h/g $Al_2O_3$, about 0.075 g DMS/h/g $Al_2O_3$, about 0.08 g DMS/h/g $Al_2O_3$, about 0.085 g DMS/h/g $Al_2O_3$, about 0.09 g DMS/h/g $Al_2O_3$, about 0.095 g DMS/h/g $Al_2O_3$, or about 0.1 g DMS/h/g $Al_2O_3$. In various other embodiments, the gas hourly space velocity may be about 0.1 g DMS/h/g $Al_2O_3$, about 0.15 g DMS/h/g $Al_2O_3$, about 0.2 g DMS/h/g $Al_2O_3$, about 0.25 g DMS/h/g $Al_2O_3$, about 0.3 g DMS/h/g $Al_2O_3$, about 0.35 g DMS/h/g $Al_2O_3$, about 0.4 g DMS/h/g $Al_2O_3$, about 0.45 g DMS/h/g $Al_2O_3$, about 0.5 g DMS/h/g $Al_2O_3$, about 0.55 g DMS/h/g $Al_2O_3$, about 0.6 g DMS/h/g $Al_2O_3$, about 0.65 g DMS/h/g $Al_2O_3$, about 0.7 g DMS/h/g $Al_2O_3$, about 0.75 g DMS/h/g $Al_2O_3$, about 0.8 g DMS/h/g $Al_2O_3$, about 0.85 g DMS/h/g $Al_2O_3$, about 0.9 g DMS/h/g $Al_2O_3$, about 0.95 g DMS/h/g $Al_2O_3$, or about 1.0 g DMS/h/g $Al_2O_3$. Weight hourly space velocity provides an indication of the capacity or size of a catalytic reactor, while its inverse provides an indication of a modified contact time (i.e., how much time the reactant is in contact with the catalyst, normalized to the mass of reactant and catalyst). True "contact time" is t [s]=V-Reactor [m3]/Volume-Flow rate [m3/s], and may be in the range of 0.01 s up to 10 s.

One of the many advantages of the recycle process of the present disclosure is that selectivity for methyl mercaptan is high, e.g., greater than about 90%. In one embodiment, the selectivity for methyl mercaptan in a single pass of the recycle process is at least about 90%. In another embodiment, the selectivity for methyl mercaptan in a single pass of the recycle process is at least about 95%. In still another embodiment, the selectivity for methyl mercaptan in a single pass of the recycle process is at least about 95%. In various embodiments, the selectivity for methyl mercaptan in a single pass of the recycle process is about 96%, about 97%, about 98%, about 99%, or about 100% percent.

As stated above, the product of the reaction taking place in the recycle reactor is an effluent gas stream comprising predominantly methyl mercaptan, hydrogen sulfide, and dimethyl sulfide. The dimethyl sulfide conversion to methyl mercaptan taking place in the recycle reactor can and will vary. In one embodiment, at least about 50 mole percent of dimethyl sulfide is converted to methyl mercaptan in a single pass. In another embodiment, from about 50 to about 80 mole percent of dimethyl sulfide is converted to methyl mercaptan in a single pass. In various embodiments, about 50, about 55, about 60, about 65, about 70, about 75, or about 80 mole percent of dimethyl sulfide is converted to methyl mercaptan in a single pass. In alternate embodiments, the conversion of dimethyl sulfide to methyl mercaptan in a single pass is about 50 to about 70 mole percent. In alternate embodiments, the conversion of dimethyl sulfide to methyl mercaptan in a single pass is about 60 to about 70 mole percent.

In embodiments where the one or more recycle gas streams comprise dimethyl ether or methanol, at least about 75 mole percent of each the dimethyl ether and methanol is converted to methyl mercaptan in a single pass. In one embodiment, at least about 75 mole percent of each the dimethyl ether and methanol is converted to methyl mercaptan in a single pass. In another embodiment, from about 75 to about 100 mole percent of each the dimethyl ether and methanol is converted to methyl mercaptan in a single pass. In various embodiments, about 75, about 80, about 85, about 90, about 95, or about 100 mole percent of each the dimethyl ether and methanol is converted to methyl mercaptan in a single pass. In alternate embodiments, the conversion of dimethyl ether and methanol to methyl mercaptan in a single pass is each about 80 to about 100 mole percent. In alternate embodiments, the conversion of dimethyl ether and methanol to methyl mercaptan in a single pass is each about 90 to about 100 mole percent. In alternate embodiments, the conversion of dimethyl ether and methanol to methyl mercaptan in a single pass is each about 95 to about 100 mole percent.

(d) Optional Downstream Processes

In some embodiments, methyl mercaptan and water are removed from the effluent gas stream, and the remaining by-products (e.g., dimethyl sulfide) and unconsumed reactants (e.g., hydrogen sulfide) may be recycled to one or more reactors (e.g., back to the recycle reactor and/or to a downstream reactor) as one or more, gas or liquid, recycle streams. Suitable separation methods are well known in the art. In other embodiments, the effluent gas stream and clean methanol are fed to a downstream reactor and reacted to produce additional methyl mercaptan.

II. Continuous Process

Another aspect of the present disclosure is a continuous process for producing methyl mercaptan. The continuous process for producing methyl mercaptan couples a recycle process to a downstream manufacturing process that produces methyl mercaptan via the methanol route. The process comprises: (a) reacting an influent gas stream comprising clean hydrogen sulfide and recycled dimethyl sulfide in a first reactor at a temperature of about 200° C. to less than 300° C. to produce a first effluent gas stream comprising methyl mercaptan, dimethyl sulfide, and hydrogen sulfide, wherein the influent gas stream comprises clean hydrogen sulfide and recycled dimethyl sulfide at a molar ratio of at least 20:1; wherein the first reactor comprises a non-promoted $Al_2O_3$ catalyst, and operates at a weight hourly space velocity of about 0.01 and 10.0 g dimethyl sulfide/hour/gram $Al_2O_3$; and wherein the methyl mercaptan is produced at a conversion of recycled dimethyl sulfide to methyl mercaptan of at least about 50 mol % and selectivity for methyl mercaptan of greater than 90%; (b) reacting the first effluent gas stream and clean liquid methanol in a second reactor to produce a second effluent gas stream comprising methyl mercaptan, dimethyl sulfide, dimethyl ether, hydrogen sulfide, and methanol, wherein the second reactor has a catalyst comprising aluminum oxide particles doped with an alkali metal; and (c) recovering at least a portion of the dimethyl sulfide from the second effluent gas stream and recycling it to step (a). The influent gas streams fed to the first reactor may further comprise recycled dimethyl ether, recycled hydrogen sulfide, recycled methanol, or any combination thereof.

The total amount of hydrogen sulfide (i.e., the clean hydrogen sulfide and, if any, recycled hydrogen sulfide) used in the continuous process is provided to the first reactor. By feeding all the hydrogen sulfide used in the continuous process to the first reactor, including that which is required for the second reactor, any minor impurities in the hydrogen sulfide gas stream will be trapped in the catalyst bed(s) of the first reactor. The catalyst bed(s) of the first reactor therefore also acts as a guard bed to prolong the performance and life of the second catalyst bed(s), which contains more expensive catalysts that are charged into multiple reactor tubes and thus more difficult, costly, and time consuming to replace.

An additional advantage of the continuous process of the present disclosure is that there is no need to obtain complete dimethyl sulfide conversion per pass because any dimethyl sulfide not converted is simply recycled back through the loop after being separated from the second effluent gas stream.

Figure 1:
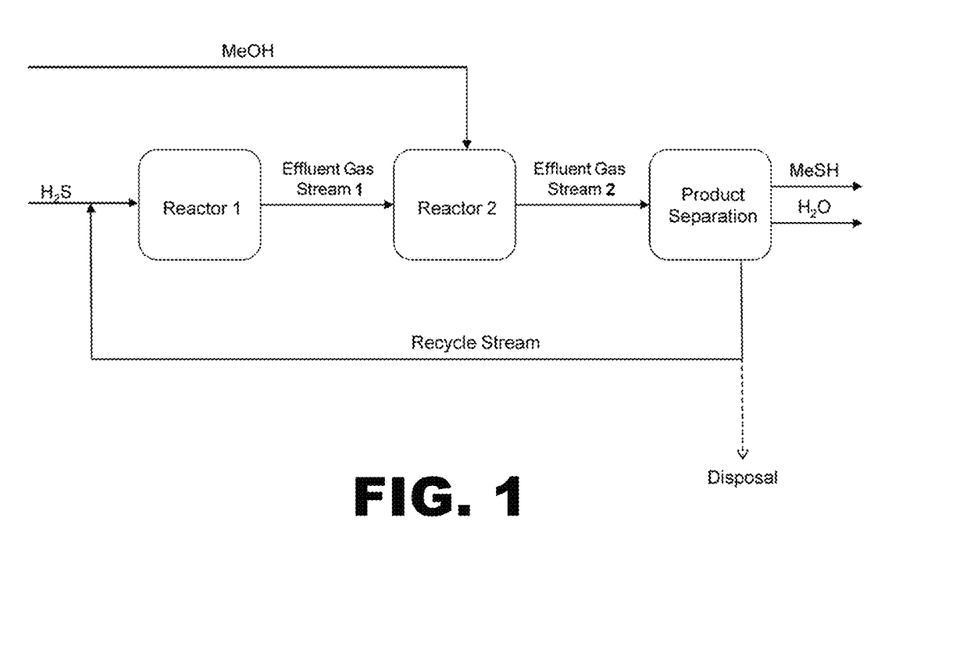
FIG. 1 depicts a process flow diagram for a continuous process for producing methyl mercaptan in accordance with an iteration of the present disclosure. Dashed lines indicate optional paths.
Figure 2:
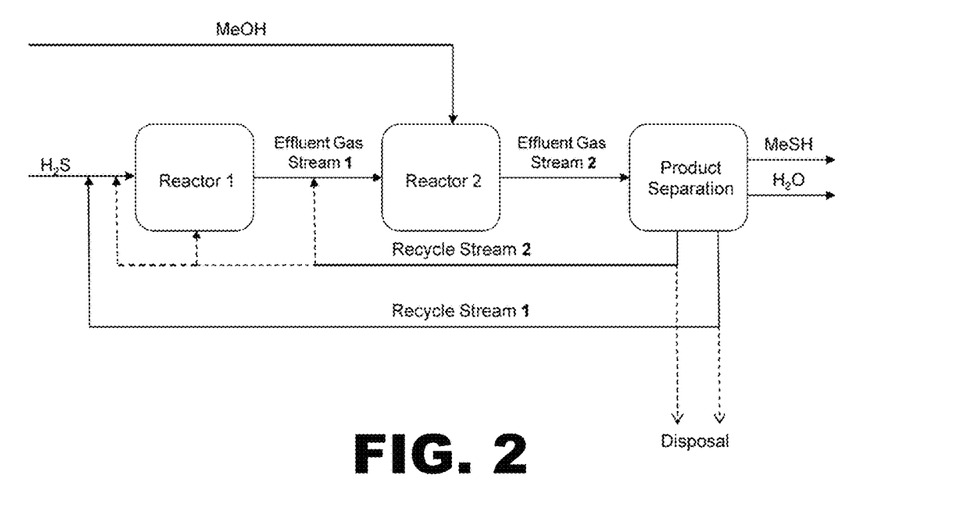
FIG. 2 depicts a process flow diagram for a continuous process for producing methyl mercaptan in accordance with an iteration of the present disclosure. Dashed lines indicate optional paths.
Figure 3:
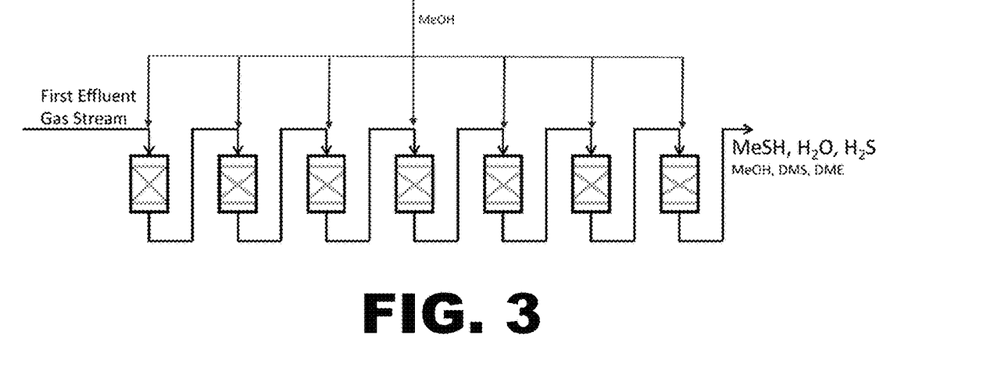
FIG. 3 depicts an embodiment of a multi-stage adiabatic reactor.

Several embodiments of the continuous process of the present disclosure are illustrated in FIG. 1 and FIG. 2.

Additional aspects of the continuous process are described in further detail below.

(a) Step (a)

Step (a) of the continuous process provide a recycle process upstream of a second reactor that produces methyl mercaptan via the methanol route. A suitable recycle process is described in detail in Section I, and the disclosures of Section I are hereby incorporated into this section by reference in their entirety.

Briefly, a recycle process comprises (a) reacting an influent gas stream comprising clean hydrogen sulfide and recycled dimethyl sulfide in a first reactor at a temperature of about 200° C. to less than 300° C. to produce a first effluent gas stream comprising methyl mercaptan, dimethyl sulfide, and hydrogen sulfide, wherein the influent gas stream comprises clean hydrogen sulfide and recycled dimethyl sulfide at a molar ratio of at least 20:1; wherein the first reactor comprises a non-promoted $Al_2O_3$ catalyst, and operates at a weight hourly space velocity of about 0.01 and 10.0 g dimethyl sulfide/hour/gram $Al_2O_3$; and wherein the methyl mercaptan is produced at a conversion of recycled dimethyl sulfide to methyl mercaptan of at least about 50 mol % and selectivity for methyl mercaptan of greater than 90%. The influent gas stream fed to the first reactor may further comprise recycled dimethyl ether, recycled hydrogen sulfide, recycled methanol, or any combination thereof.

The amount of each recycled reactant provided to the recycle reactor may vary depending upon reaction conditions (e.g., temperature, weight hourly space velocity, etc.), provided the $H_2S$:DMS feed ratio is at least 20:1. For example, the $H_2S$:DMS feed ratio may be 20:1, 25:1, 30:1, 35:1, 40:1, 45:1, 50:1, 55:1, 60:1, or higher. In some embodiments, recycled dimethyl sulfide is the only recycle reactant provided to the recycle other. In other embodiments, recycled methanol and/or recycled dimethyl ether are also provided to the recycle reactor in molar ratio of methanol or dimethyl ether to dimethyl sulfide that is less than 2.3, preferably less than 1.0, more preferably less than 0.3. In embodiments where recycled hydrogen sulfide is provided to the recycled reactor, the amount of clean hydrogen sulfide gas may be reduced proportionately to achieve the desired $H_2S$:DMS feed ratio. The dimethyl sulfide, dimethyl ether, and methanol conversion to methyl mercaptan taking place in the first reactor may be at least about 50 mol %, at least about 75 mol %, and at least about 75 mol %, respectively, while achieving selectivity for methyl mercaptan that is greater than 90% for each reactant. In various embodiments, the temperature of the first reactor may be between about 200° C. to about 280° C., between about 220° C. to about 280° C., between about 240° C. to about 280° C., between about 220° C. to about 250° C., or between about 240° C. to about 270° C., and the operating pressure of the first reactor may be between about 1 and about 40 bar, between about 10 and about 40 bar, or between about 10 and about 20 bar.

(b) Step (b)

The effluent gas stream from the recycle process (i.e., the first effluent gas stream) and clean liquid methanol are fed into a second reactor comprising a second catalyst. As used herein, the term "clean liquid methanol" refers to liquid methanol that has not been previously used in a manufacturing process for producing methyl mercaptans (i.e., not recycled). A recycle gas stream, for example, a recycle gas stream comprising recycled methanol, may also be fed into the second reactor or combined with the first effluent gas stream upstream of the second reactor.

Catalysts suitable for converting methanol and hydrogen sulfide to methyl mercaptan with a high conversion and selectivity are known in the art. The catalyst support used may be silicates, titanium oxides, zeolites, aluminas, aluminium oxides. Preferably the catalyst support is doped with an alkali metal including, but not limited to $K_2CO_3$, $K_2WO_4$, and $Cs_2WO_4$. In an exemplary embodiment, the catalyst of the second reactor comprises aluminum oxide particles and potassium tungstate ($K_2WO_4/Al_2O_3$). The total loading of potassium tungstate on the aluminum oxide particles is about 10 wt. % to about 40 wt. %, preferably about 10 wt. % to about 30 wt. %, or more preferably about 10 wt. % to about 20 wt. %. In various embodiments, the total loading of potassium tungstate on the aluminum oxide particles is about 10 wt %, about 11 wt %, about 12 wt %, about 13 wt %, about 14 wt %, about 15 wt %, about 16 wt %, about 17 wt %, about 18 wt %, about 19 wt %, or about 20 wt %. The catalyst is generally in the solid phase and may be in a variety of forms such as pellets, spheres, or rings. The catalyst may optionally be mixed with inert carriers such as silica, silicates, titanium dioxide, or zirconium oxides.

The aluminum oxide particles have an alumina surface area between 100 $m^2/g$ and 500 $m^2/g$, and particle size of 1.5-5 mm. In some embodiments, the aluminum oxide particles have an alumina surface area between about 150 $m^2/g$ and 500 $m^2/g$, between about 200 $m^2/g$ and 500 $m^2/g$, or between 250 $m^2/g$ and 500 $m^2/g$. In other embodiments, the aluminum oxide particles have an alumina surface area between about 100 $m^2/g$ and 450 $m^2/g$, between about 150 $m^2/g$ and 450 $m^2/g$, or between about 200 $m^2/g$ and 450 m²/g. In an exemplary embodiment, the aluminum oxide particles have an alumina surface area between about 200 m²/g and about 250 m²/g. The pore size of the particles may range between about 2 nm to about 20 nm, or between about 5 nm and 15 nm. Alternatively, alumina particles with a bimodal pore size distribution may be used. For example, a catalyst may contain particles with a pore size of between 2 nm to 20 nm and particles with a pore size between about 50 nm to about 1 μm. The catalyst may optionally be mixed with inert carriers such as silica, silicates, titanium dioxide, or zirconium oxides.

Alkali doped $Al_2O_3$ catalysts of the present disclosure may be prepared according methods well known in the art. Optimal promoter loading should result in a methyl mercaptan selectivity that is about 90%. In this regard, alkali loading is preferably greater than 5 μmol/m² alumina. For example, when the catalyst is $K_2WO_4/Al_2O_3$, the precursor (e.g., $K_2WO_4$) is dissolved in a suitable solvent and then applied to the support (e.g., $Al_2O_3$) in one or more impregnation steps, followed by a calcination step. Sulfidation of the catalyst can be accomplished prior to adding the catalyst to the reactor or it can be accomplished in the reaction itself. Each impregnation step comprises admixing the support with the dissolved precursor, a predrying step to allow the initial concentration gradient over the cross section of the shaped bodies to be substantially balanced, and then a final drying step.

The second reactor may be multi-tubular reactor or an adiabatic reactor. In typical operation of a tubular reactor, a heat transfer fluid, such as a molten salt bath, may be used to transfer heat during methyl mercaptan production. Any transfer fluid used in this process should be stable at the temperatures of reaction. In certain embodiments, the second reactor is a multi-stage adiabatic reactor comprising two or more catalyst stages. For example, the second reactor may have two, three, four, five, six, seven, eight, nine, ten or more stages. Each catalyst stage of the multi-stage adiabatic reactor contains a catalyst bed. In some embodiments, the same catalyst is used at each stage. In other embodiments, different catalysts are used at each stage. A portion of the clean, liquid methanol fed to the second reactor is mixed with a gas feed stream before each catalyst stage. In this manner, heat from the gas feed stream evaporates the liquid methanol and the resultant gas mixture entering the catalyst stage has a lower temperature than the gas feed stream from which it was produced. For the first catalyst stage, the gas feed stream may be the first effluent gas stream, or the first effluent gas stream combined with a recycle gas. For each subsequent catalyst stage, a portion of the total amount of the clean, liquid methanol fed to the second reactor is mixed with the effluent gas from the preceding stage.

The reaction conditions, namely temperature and pressure, in the second reactor can and will vary. In this regard, the temperature in the second reactor is generally about 250° C. to about 400° C., preferably about 260° C. to about 360° C. The temperature at the reactor inlet and outlet can and will vary. Particularly when the second reactor is an adiabatic reactor, the outlet temperature is greater than the inlet temperature.

The overall operating pressure of the second reactor also can and will vary. A suitable operating pressure of the second reactor is generally about 30 bar or less. For example, the operating pressure of the second reactor may be about 5 bar, about 10 bar, 15 bar, about 20 bar, about 25 bar, or about 30 bar. Alternatively, the operating pressure of the second reactor may be about 5 to about 20 bar. The operating pressure of the second reactor may also be about 10 to about 20 bar. In various embodiments, the operating pressure of the second reactor may be about 10, about 11 about 12, about 13, about 14, about 15, about 16, about 17, about 18, about 19 or about 20 bar.

Flow rates may be varied to achieve the desired contact times between the catalyst and substrates. In various embodiments, flow rates may be varied to achieve a methyl mercaptan formation rate of about 0.2 to about 1.0 kg MeSH/hr/kg alkali doped $Al_2O_3$ at a temperature of about 250° C. to about 400° C.

The selectivity for methyl mercaptan in the second reactor is typically greater than about 90%. In one embodiment, the selectivity for methyl mercaptan in a single pass is at least about 90%. In another embodiment, the selectivity for methyl mercaptan in a single pass is at least about 95%. In still another embodiment, the selectivity for methyl mercaptan in a single pass is at least about 95%. In various embodiments, the selectivity for methyl mercaptan in a single pass of the recycle process is about 96%, about 97%, about 98%, or about 99%.

As stated above, the product of the reaction taking place in the second reactor is a second effluent gas stream comprising predominantly methyl mercaptan and water. Unreacted hydrogen sulfide and methanol may also be present, as may be the by-products dimethyl sulfide and dimethyl ether. The methanol conversion to methyl mercaptan taking place in the second reactor can and will vary. In one embodiment, at least about 85 mole percent of methanol is converted to methyl mercaptan in a single pass. In another embodiment, from about 85 to about 95 mole percent of the methanol is converted to methyl mercaptan in a single pass. In another embodiment, from about 90 to about 100 mole percent of the methanol is converted to methyl mercaptan in a single pass. In various embodiments, about 90, about 91, about 92, about 93, about 94, about 95, about 96, about 97, about 98, about 99 mole percent of each the methanol is converted to methyl mercaptan in a single pass.

(c) Step (c)

After methyl mercaptan and water are removed from the second effluent gas stream, the remaining by-products (e.g., dimethyl sulfide and dimethyl ether) and unconsumed reactants (e.g., methanol and hydrogen sulfide) may be recycled to the first reactor as one or more, gas or liquid, recycle streams. Suitable separation methods are well known in the art. The amount of each by-product and unconsumed reactant that is recycled may vary in order to provide a desired molar ratio of reactants in step (a).

In some embodiments, at least a portion of the dimethyl sulfide from the second effluent gas stream is recovered and recycled to step (a). For example, at least 5%, at least 10%, at least 20%, at least 30%, at least 40%, at least 50%, at least 60%, at least 70%, at least 80%, or at least 90% of the dimethyl sulfide from the second effluent gas stream is recovered and recycled to step (a). In other embodiments, about 100% of the dimethyl sulfide from the second effluent gas stream is recovered and recycled to step (a).

In various embodiments, at least a portion of the dimethyl ether from the second effluent gas stream is recovered and recycled to step (a). For example, at least 5%, at least 10%, at least 20%, at least 30%, at least 40%, at least 50%, at least 60%, at least 70%, at least 80%, at least 90%, or 100% of the dimethyl sulfide from the second effluent gas stream is recovered and recycled to step (a).

In various embodiments, at least a portion of the hydrogen sulfide from the second effluent gas stream is recovered and recycled to step (a). For example, at least 5%, at least 10%, at least 20%, at least 30%, at least 40%, at least 50%, at least 60%, at least 70%, at least 80%, at least 90%, or 100% of the dimethyl sulfide from the second effluent gas stream is recovered and recycled to step (a).

In various embodiments, at least a portion of the methanol from the second effluent gas stream is recovered and recycled to step (a). For example, at least 5%, at least 10%, at least 20%, at least 30%, at least 40%, at least 50%, at least 60%, at least 70%, at least 80%, at least 90%, or 100% of the dimethyl sulfide from the second effluent gas stream is recovered and recycled to step (a).

III. Illustrative Embodiment of a Continuous Process for Producing Methyl Mercaptan FIG. 4 discussed below provides an example of an iteration of the disclosure for producing methyl mercaptan in a continuous process. This example is one of several iterations of the present invention and should not be construed as limiting the invention's scope. An alternative iteration is presented in FIG. 5.

Figure 4:
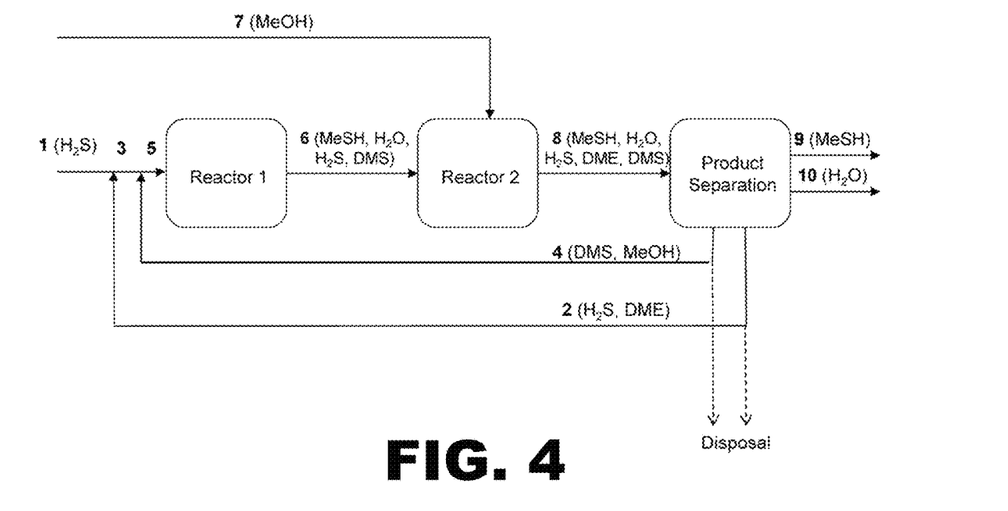
FIG. 4 depicts a process flow diagram for a continuous process for producing methyl mercaptan in accordance with an iteration of the present disclosure. Dashed lines indicate optional paths.
Figure 5:
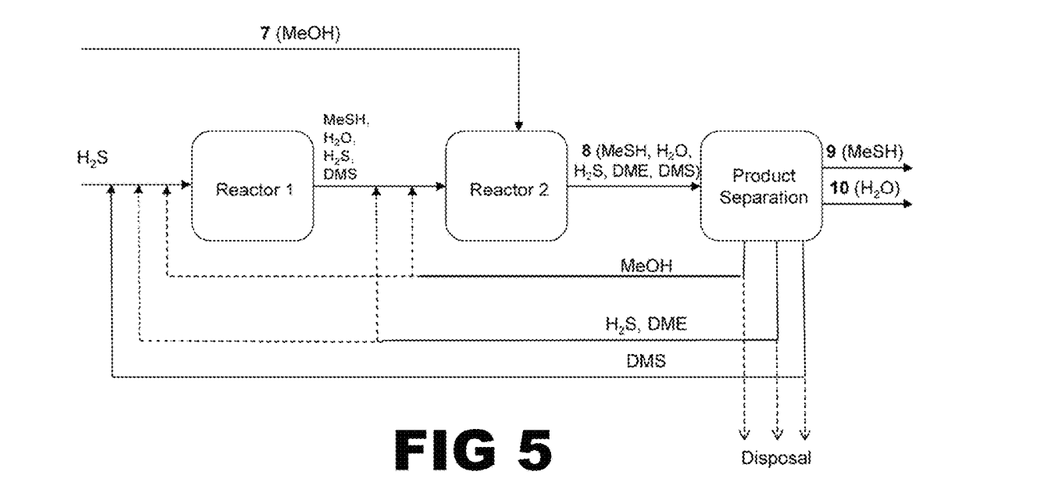
FIG. 5 depicts a process flow diagram for a continuous process for producing methyl mercaptan in accordance with an iteration of the present disclosure. Dashed lines indicate optional paths.

With reference to FIG. 4, a clean hydrogen sulfide gas stream 1 is mixed with a recycled gas stream 2 containing recycled hydrogen sulfide and recycled dimethyl sulfide to produce gas stream 3 that has a molar ratio of hydrogen sulfide to dimethyl sulfide that is greater than 20:1 and less than 60:1. Recycled stream 4 is a liquid that contains recycled methanol and recycled dimethyl sulfide in a molar ratio that is less than 0.3. Recycled stream 4 is atomized and injected into gas stream 3 to produce a resultant gas stream 5. Gas stream 5 is then fed to Reactor 1 at a weight hourly space velocity of about 0.01 to 10.0 g DMS/h/g Al$_2$O$_3$, where at least 95 mol % of the methanol, at least 95 mol % of the dimethyl ether, and about 50 to about 70 mol % of the dimethyl sulfide is converted into methyl mercaptan, water, and various by-products over a non-promoted, Al$_2$O$_3$ catalyst at about 240° C. to about 250° C. The catalyst has an alumina surface area between about 200 m$^2$/g and about 250 m$^2$/g, and particle size of about 1.5 mm to about 5 mm. The selectivity for the methyl mercaptan in Reactor 1, a single stage adiabatic reactor, is greater than 95%. The reaction effluent gas stream 6 comprises methyl mercaptan, water, unreacted hydrogen sulfide, and unreacted dimethyl sulfide.

Reaction effluent gas stream 6 enters Reactor 2, which is a multi-stage adiabatic reactor with n stages, where n=7-10. Each stage has a catalyst bed and the catalyst in each stage is the same. The catalyst is potassium tungstate on an aluminum oxide particle. The catalyst has an alumina surface area between about 200 m$^2$/g and about 250 m$^2$/g, and particle size of about 1.5 mm to about 5 mm. The total loading of potassium tungstate on the alumina is expected to be about 15.1 wt %. Liquid methanol 7 also enters Reactor 2 where it is divided into m portions (m=n). A first portion of liquid methanol is injected into the effluent gas stream 6 before entering the catalyst bed of the first stage, a second portion of liquid methanol is injected before the second stage, etc. The reaction in Reactor 2 occurs at about 280° C. to about 380° C. About 95 mol % of the methanol is converted to methyl mercaptan, and the selectivity is at least about 90%. The reaction effluent gas stream 8 comprises methyl mercaptan, water, hydrogen sulfide, dimethyl sulfide, dimethyl ether and methanol.

Methyl mercaptan 9 and water 10 are removed from reaction effluent gas stream 8 by one or more downstream steps (Product Separation). The remaining components of reaction effluent gas stream 8 are disposed of, or recycled as recycled gas stream 2 or recycled gas stream 4. The amount of dimethyl sulfide, methanol, hydrogen sulfide and dimethyl ether that is recycled may vary in order to provide the desired molar ratio of reactants described above.

The following examples are included to demonstrate preferred embodiments of the disclosure. It should be appreciated by those of skill in the art that the techniques disclosed in the examples that follow represent techniques discovered by the inventors to function well in the practice of the disclosure. Those of skill in the art should, however, in light of the present disclosure, appreciate that changes may be made in the specific embodiments that are disclosed and still obtain a like or similar result without departing from the spirit and scope of the disclosure. Therefore, all matter set forth or shown in the accompanying drawings is to be interpreted as illustrative and not in a limiting sense.

EXAMPLES

The following examples illustrate various iterations of the disclosure.

Example 1: Dimethyl Sulfide Conversion to Methyl Mercaptan

The results from several iterations of the recycle process are provided in the table below. In each experiment, the recycle reactor is one adiabatic reactor stage with a fixed bed of crushed Al$_2$O$_3$ pellets diluted with inerts. Reactants consisted of hydrogen sulfide and dimethyl sulfide in the amounts indicated. The inlet temperature of the reactor in each experiment is 240° C. Temperature was controlled by hot oil heating and measured along vertical axis. The pressure of the inlet flow to the reactor was set by pressure valve, and the component flows set by hydrogen sulfide flow control and methanol/dimethyl sulfide pump. The composition of the product flowing from the reactor was measured by gas chromatography (GC).

As shown in experiment number HP5-3, no dimethyl sulfide was converted to methyl sulfide in the presence of methanol (2.3 mol/mol MeOH:DMS) despite a very low weight hourly space velocity. In contrast, with a 10-fold higher weight hourly space velocity factor, 10% dimethyl sulfide conversion was achieved in absence of methanol (see HP5-14). In these experiments, about 50% dimethyl sulfide conversion was achieved with a weight hourly space velocity of 0.2 to 0.3 g DMS/h/g catalyst and a hydrogen sulfide to dimethyl sulfide molar ratio of 26 to 55.

| Experiment No. | Pressure [bara] | H$_2$S/DMS [mol/mol] | MeOH/DMS [mol/mol] | WHSV [g$_{DMS}$/h/g$_{Cat}$] | 1/WHSV [h g$_{Cat}$/g$_{DMS}$] | Temp. [° C.] | DMS conv. [mol-%] |
|---|---|---|---|---|---|---|---|
| Influence of H$_2$S/DMS ratio | | | | | | | |
| HP5-7 | 15 | 26 | 0 | 0.21 | 4.83 | 240 | 72% |
| HP5-6 | 15 | 52 | 0 | 0.21 | 4.81 | 240 | 67% |
| HP5-8 | 15 | 60 | 0 | 0.22 | 4.65 | 240 | 71% |

-continued

| Experiment No. | Pressure [bara] | H$_2$S/DMS [mol/mol] | MeOH/DMS [mol/mol] | WHSV [g$_{DMS}$/h/g$_{Cat}$] | 1/WHSV [h g$_{Cat}$/g$_{DMS}$] | Temp. [° C.] | DMS conv. [mol-%] |
|---|---|---|---|---|---|---|---|
| Influence of MeOH/DMS ratio | | | | | | | |
| HP5-3 | 15 | 107 | 2.3 | 0.10 | 9.62 | 240 | 0% |
| Influence of pressure (compare HP5-6) | | | | | | | |
| HP5-9 | 10 | 55 | 0 | 0.20 | 5.08 | 240 | 78% |
| HP5-10 | 17 | 55 | 0 | 0.20 | 5.13 | 240 | 68% |
| Influence of WHSV (compare HP5-10) | | | | | | | |
| HP5-14 | 17 | 55 | 0 | 1.00 | 1.00 | 240 | 10% |
| HP5-15 | 17 | 55 | 0 | 0.33 | 3.00 | 240 | 48% |
| New process design | | | | | | | |
| HP5-11 | 17 | 28 | 0 | 0.39 | 2.56 | 240 | 51% |
| HP5-12 | 17 | 18 | 0 | 0.62 | 1.63 | 240 | 42% |
| HP5-13 | 17 | 12 | 0 | 0.91 | 1.10 | 240 | 38% |

Example 2: Dimethyl Sulfide Conversion to Methyl Mercaptan

Figure 6:
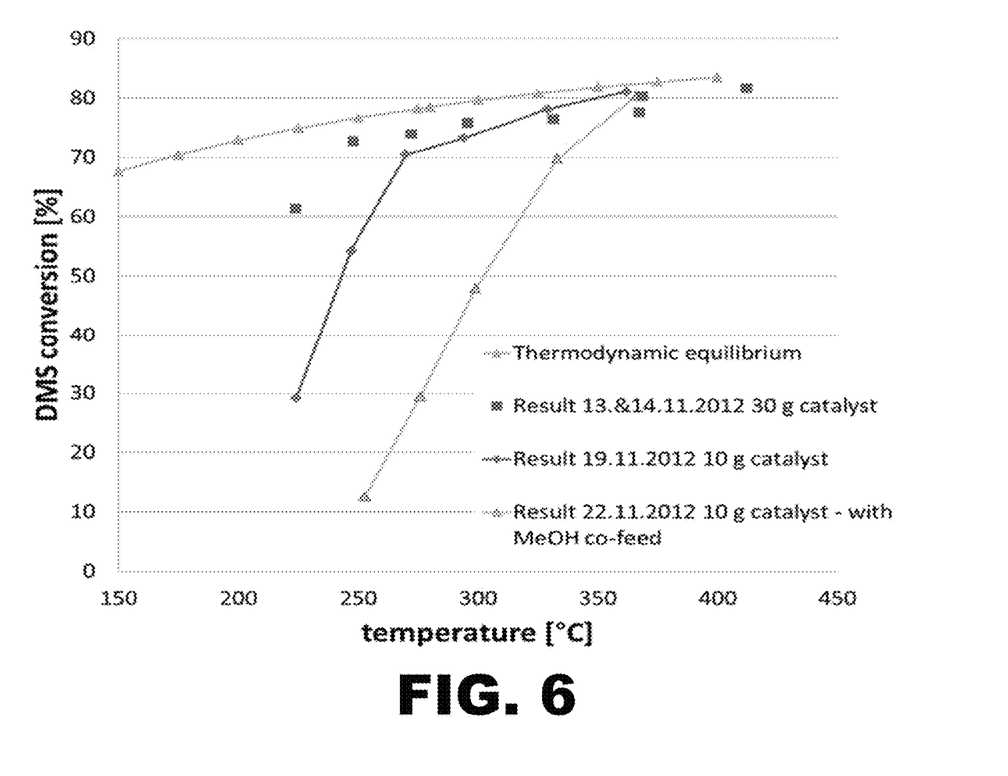
FIG. 6 depicts a graph illustrating the percent conversion of dimethyl sulfide to methyl mercaptan when reacted over a non-promoted, $Al_2O_3$ catalyst.
Figure 7:
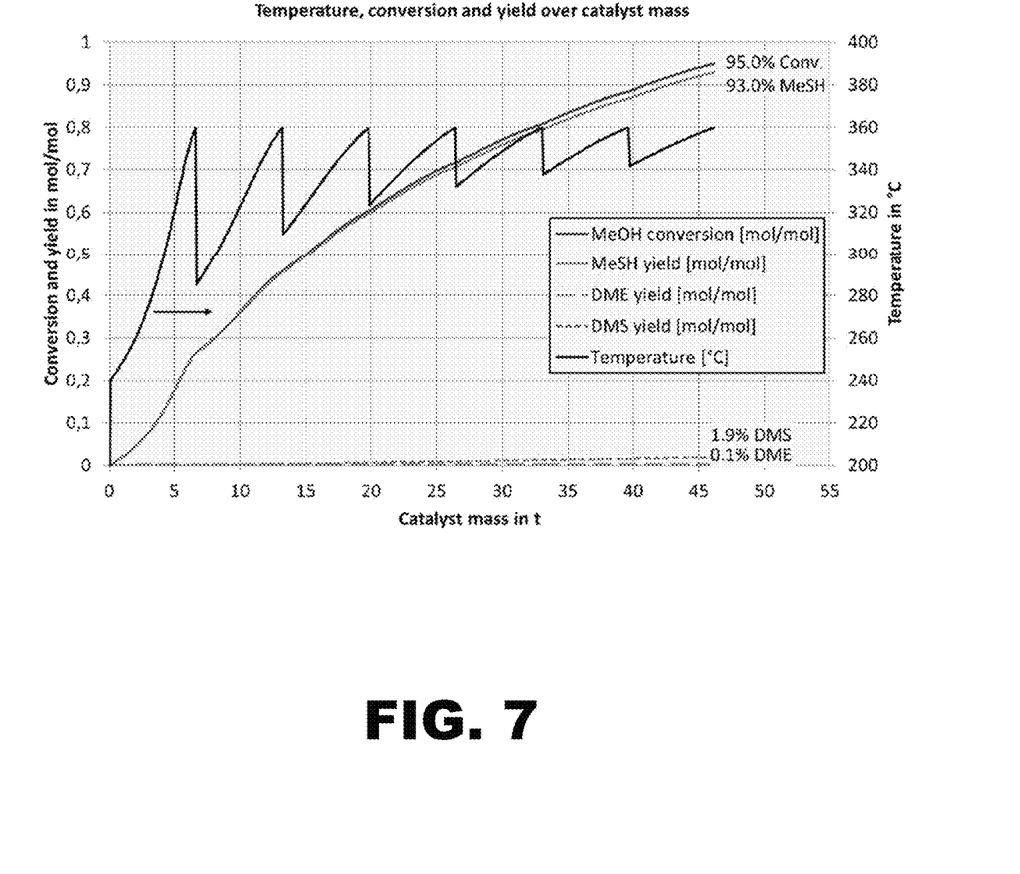
FIG. 7 depicts a graph illustrating a simulation showing the percent conversion of methanol to methyl mercaptan and yield of methanol mercaptan when methanol is reacted over a $K_2WO_4/Al_2O_3$ catalyst in an adiabatic reactor with seven stages.

The results from several iterations of the recycle process are illustrated in FIG. 6. In each experiment, the recycle reactor is one adiabatic reactor stage with a fixed bed of spherical Al$_2$O$_3$ pellets. The inlet temperature of the reactor in each experiment is 240° C. and the reaction occurred at atmospheric pressure. Reactants consisted of hydrogen sulfide and dimethyl sulfide in a 20:1 molar ratio (red square and blue rhombus) or hydrogen sulfide, dimethyl sulfide, and methanol, where the molar ratio of hydrogen sulfide to dimethyl sulfide is 20:1 and the molar ratio of methanol to dimethyl sulfide is 0.3 (yellow triangle). The weight hourly space velocity in each experiment was 1 g DMS/h/g catalyst (blue rhombus), 0.33 g DMS/h/g catalyst (red square), and 0.86 g DMS/h/g catalyst (yellow triangle). Thermodynamically limited dimethyl sulfide conversion is shown by green triangles.

In Example 1, no dimethyl sulfide was converted to methyl sulfide in the presence of methanol (2.3 molar ratio of methanol to dimethyl sulfide) despite a weight hourly space velocity of 1 g DMS/h/g. The data in shown in FIG. 6 also show, surprisingly, that even small amounts of methanol (e.g. 0.3 molar ratio of methanol to dimethyl sulfide) negatively affects dimethyl sulfide conversion at low temperatures, such that higher temperatures are required to get same conversion as in absence of methanol.

What is claimed is:

1. A continuous process for producing methyl mercaptan, the process comprising
   (a) reacting an influent gas stream comprising clean hydrogen sulfide and recycled dimethyl sulfide in a first reactor under conditions to produce a first effluent gas stream, wherein the first effluent gas stream comprises methyl mercaptan and hydrogen sulfide; and wherein the methyl mercaptan is produced at a conversion of recycled dimethyl sulfide to methyl mercaptan of at least about 50 mol % and selectivity for methyl mercaptan of greater than 90%; wherein the first reactor comprises a non-promoted Al$_2$O$_3$ catalyst; and wherein the first reactor has a temperature of about 200° C. to about 250° C.;
   (b) reacting the first effluent gas stream and clean liquid methanol in a downstream second reactor under conditions to produce a second effluent gas stream that comprises methyl mercaptan and dimethylsulfide; and
   (c) recovering at least a portion of the dimethylsulfide from the second effluent gas stream and recycling it to the first reactor of step (a).

2. The process of claim 1, wherein the first reactor operates at a weight hourly space velocity of about 0.01 and 10.0 g dimethyl sulfide/hour/gram Al$_2$O$_3$.

3. The process of claim 1, wherein the conversion of dimethyl sulfide to methyl mercaptan in step (a) is about 60 mol % to about 70 mol % and the selectivity for methyl mercaptan is greater than 95%.

4. The process of claim 1, wherein the second reactor is an adiabatic reactor that has two or more catalyst stages, and the catalyst in each stage comprises aluminum oxide particles and potassium tungstate, and wherein a portion of the total amount of clean liquid methanol is introduced upstream of each catalyst stage.

5. The process of claim 1, wherein the second reactor has a temperature of about 250° C. to about 400° C.

6. The process of claim 1, wherein the clean liquid methanol conversion to methyl mercaptan in step (b) is at least 85 mol % and the selectivity for methyl mercaptan is greater than 90%.

7. The process of claim 1, wherein the first reactor is an adiabatic reactor with a single catalyst stage.

8. A continuous process for producing methyl mercaptan, the process comprising reacting an influent gas stream comprising clean hydrogen sulfide and dimethyl sulfide recycled from a downstream methanol route reactor in a recycle reactor under conditions to produce a first effluent gas stream, wherein the first effluent gas stream comprises methyl mercaptan and hydrogen sulfide; and wherein the methyl mercaptan is produced at a conversion of recycled dimethyl sulfide to methyl mercaptan of at least about 50 mol % and selectivity for methyl mercaptan of greater than 90%, further comprising reacting the first effluent gas stream and clean liquid methanol in the downstream methanol route reactor; and wherein the recycle reactor comprises a non-promoted Al$_2$O$_3$ catalyst.

9. The process of claim 8, wherein the temperature of the recycle reactor is about 200° C. to 250° C.

10. The process of claim 8, wherein the clean hydrogen sulfide and the recycled dimethyl sulfide are at a molar ratio of at least 20:1.

11. The process of claim 8, wherein the recycle reactor comprises a Al$_2$O$_3$ catalyst and operates at a weight hourly space velocity of about 0.01 and 10.0 g dimethyl sulfide/hour/gram Al$_2$O$_3$.

12. The process of claim 8, wherein the conversion of dimethyl sulfide to methyl mercaptan is about 60 mol % to about 70 mol % and the selectivity for methyl mercaptan is greater than 95%.

* * * * *